(12) United States Patent
Peters

(10) Patent No.: US 11,232,866 B1
(45) Date of Patent: Jan. 25, 2022

(54) VEIN THROMBOEMBOLISM (VTE) RISK ASSESSMENT SYSTEM

(71) Applicant: Acorai AB, Domsten (SE)

(72) Inventor: Filip Ludwig Peters, Domsten (SE)

(73) Assignee: Acorai AB, Domsten (SE)

( * ) Notice: Subject to any disclaimer, the term of this patent is extended or adjusted under 35 U.S.C. 154(b) by 0 days.

(21) Appl. No.: 17/099,772

(22) Filed: Nov. 16, 2020

(51) Int. Cl.
*A61B 5/00* (2006.01)
*G16H 50/30* (2018.01)
*G16H 40/67* (2018.01)
*G16H 80/00* (2018.01)
*G06F 3/01* (2006.01)
*G06T 7/00* (2017.01)
*G06K 9/00* (2006.01)
*A61B 5/024* (2006.01)
*A61B 5/0205* (2006.01)
*A61B 7/04* (2006.01)

(52) U.S. Cl.
CPC ........... *G16H 50/30* (2018.01); *A61B 5/0024* (2013.01); *A61B 5/0205* (2013.01); *A61B 5/02416* (2013.01); *A61B 5/6898* (2013.01); *A61B 5/72* (2013.01); *A61B 5/7264* (2013.01); *A61B 5/7275* (2013.01); *G06F 3/015* (2013.01); *G06K 9/00536* (2013.01); *G06T 7/0012* (2013.01); *G16H 40/67* (2018.01); *G16H 80/00* (2018.01); *A61B 7/04* (2013.01); *G06T 2207/30101* (2013.01)

(58) Field of Classification Search
CPC ........ G16H 50/30; G16H 80/00; G16H 40/67; A61B 5/6898; A61B 5/0205; A61B 5/7275; A61B 5/7264; A61B 5/72; A61B 5/0024; A61B 5/02416; A61B 7/04; G06T 7/0012; G06T 2207/30101; G06F 3/015; G06K 9/00536
See application file for complete search history.

*Primary Examiner* — Rex R Holmes
(74) *Attorney, Agent, or Firm* — Silver Legal LLC; Jarrett L. Silver

(57) ABSTRACT

A vein thromboembolism (VTE) risk assessment system that includes a casing having a shape adapted to secure a plurality of components with the casing. The casing includes a microphonic sensor, a Photoplethysmography (PPG) sensor, an Inertial Measurement Unit (IMU) sensor, a diaphragm, and a microcontroller. The microphonic sensor captures VTE audio signals indicative of the VTE risk of the user. The PPG sensor measures blood volume changes in a skin area in response to venous hemodynamic changes in a lower limb. The IMU sensor captures seismic signals indicative of the VTE risk of the user. The diaphragm enhances auscultation signals. The microcontroller transmits data to a computing device.

30 Claims, 14 Drawing Sheets

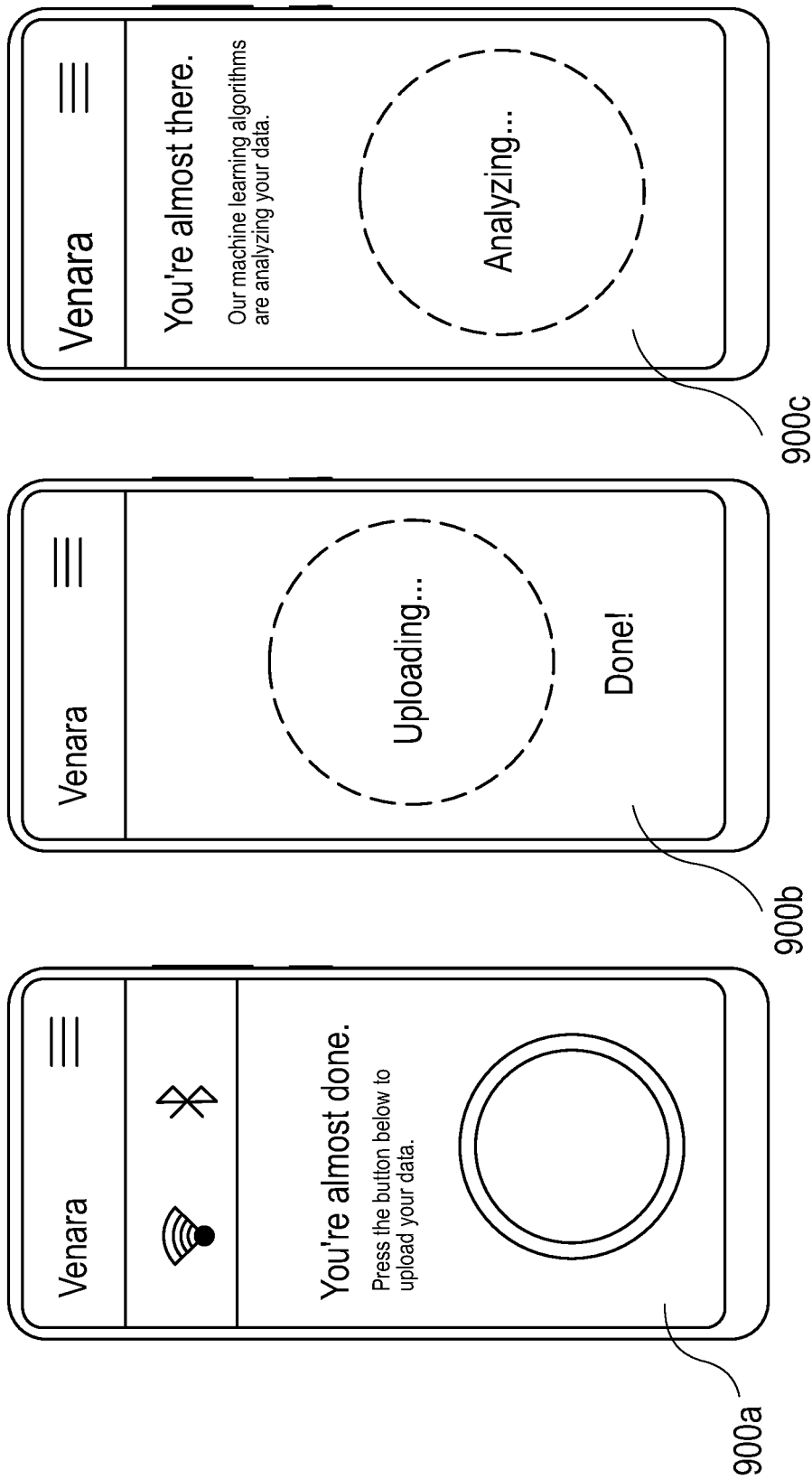

VEIN THROMBOEMBOLISM (VTE) RISK ASSESSMENT SYSTEM

CROSS-REFERENCES TO RELATED PATENT APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND

Technical Field

The inventive subject matter is generally directed towards vein thromboembolism (VTE) risk assessment systems and methods. More particularly embodiments are related to, but not limited to, a vein thromboembolism (VTE) risk assessment system for analyzing and detecting vein thromboembolism (VTE).

Description of the Related Art

Currently, Artificial intelligence (AI) and machine learning (ML) have been used in the big data analysis to provide outputs without human intervention in various healthcare services, such as bioinformatics, genomics, and image analysis. Artificial intelligence (AI) has the potential to impact almost every aspect of healthcare, from detection to prediction and prevention of patients from acute medical illnesses.

Typically, acute medical illness has an increased risk of venous thromboembolism (VTE). Venous thromboembolism (VTE) is caused by a thrombus (blood clot) forms within a vein. The blood clots can occur in either the deep or the superficial veins of the body. However, the blood clots within the deep venous system (deep venous thrombosis-DVTs) are most concerning due to the risk of pulmonary embolus (PE), where part of the blood clot breaks off and travels to the lungs, restricting gas exchange within that area. DVTs frequently occur in the deep veins of the legs, where they may be asymptomatic or may cause pain and swelling of the affected leg. Long-term they can lead to post-thrombotic syndrome, which can result in considerable morbidity from chronic pain and swelling of the affected limb.

While venography is a common clinical tool for diagnosing deep vein thrombosis, it suffers from being invasive and a relatively high-risk method. A duplex scan is another diagnostic tool commonly used in clinical practice. The existing diagnostic procedures are expensive, time-consuming, and can be carried out only in the hospital settings by a skilled technician.

Although AI and ML provide opportunities in the diagnosis and treatment of VTE, there still may be challenges and pitfalls related to various safety and hygiene concerns. When a patient first experiences symptom of an illness such as VTE and subsequently begins to seek clinical treatment, the situation is very often quite far progressed and serious. It is therefore desirable to provide a system that can detect and continuously monitor the patient and detect in realtime the potential progression of deep vein thrombosis in at-risk patients such as patients in acute care and/or post-acute settings. Further, there is a need for a safe system that can utilize AI and ML to facilitate the patients to detect VTE in the absence of medical practitioners. There is furthermore a need for a portable VTE risk assessment system that can aid in analyzing and detecting VTE. In view of the above, there is a long-felt need in the healthcare industry to address the described issues.

SUMMARY

Vein thromboembolism (VTE) risk assessment systems for use with a handheld electronic device (HED) is provided and shown in and/or described in connection with the figures.

One aspect of the inventive subject matter relates to a VTE risk assessment system, specifically a HED having a casing with a shape adapted to secure a plurality of components with said casing. The casing includes a microphonic sensor, a Photoplethysmography (PPG) sensor, an Inertial Measurement Unit (IMU) sensor, a diaphragm, and a microcontroller. The microphonic sensor is configured to capture VTE audio signals indicative of the VTE risk of the user. The PPG sensor is configured to measure blood volume changes in a skin area in response to venous hemodynamic changes in a limb such as a lower limb. The IMU sensor is configured to capture seismic signals indicative of the VTE risk of the user. The diaphragm is configured to enhance auscultation signals. The microcontroller is configured to transmit data received from the microphonic sensor, the PPG sensor, and the IMU sensor to a computing device. The computing device is configured to receive, in one or more temporal windows, a representation of one or more of the IMU sensor, the PPG sensor, and the microphonic sensor signal recorded by the casing. The computing device is configured to use the received data to analyze features of the IMU sensor, the PPG sensor, and the microphonic sensor. In several embodiments, the data used for the analysis is from one or more portions of the received representations falling within each of the one or more temporal windows. The computing device is configured to use sensor data to identify patterns of the features of respective sensors from within the one or more portions based on at least one of the following: a classification model and a regression model. The computing device is configured to calculate, basis the identified patterns, a probability of whether one or more portions correspond to the VTE of a user.

In an embodiment, the PPG sensor generates infrared (IR) light to measure blood volume changes in the skin area in response to venous hemodynamic changes in the lower limb.

In an embodiment, the casing is configured to capture VTE risk data of the user when positioned against the chest of the user.

In an embodiment, the casing is configured to capture VTE risk data of the user when positioned against the thoracic cage of the user.

In an embodiment, the casing is configured to capture VTE risk data of the user when positioned against the back cage of the user.

In an embodiment, the computing device comprises a processor to execute a plurality of instructions pertaining to a VTE risk monitoring application, wherein the processor is configured to display one or more commands to determine the positioning of the casing on the user's body.

In an embodiment, the classification model is trained to detect VTE.

In an embodiment, the classification model is trained based on the detected features of the IMU sensor.

In an embodiment, the casing further comprises a heat-sensing camera to detect variations in the skin area temperature resulting from variations in the blood volume changes in the skin area in response to venous hemodynamic changes in the lower limb.

In an embodiment, the diaphragm comprises an enhancer unit to amplify low-frequency auscultation signals pertaining to the VTE audio signals.

In an embodiment, the casing further comprises a battery configured to supply electrical power to the circuit board.

The VTE risk assessment system includes a second handheld electronic device worn by the user, comprising sensors to collect patient health data, wirelessly connected with the system, further comprising a wireless transceiver configured to establish a communication with the computing device to transmit VTE risk data therebetween. The computing device is configured to: detect, based on the classification model, VTE.

The VTE risk assessment system may include a second handheld electronic device worn by the user, comprising sensors to collect patient health data, wirelessly connected with the system, further comprising a wireless transceiver configured to establish a communication with the computing device to transmit VTE risk data therebetween.

The computing device is configured to: detect, based on the classification model, VTE;

and estimate, based on the regression model, the severity of VTE.

The casing is configured as a patch with the ability to adhere to the patient's body.

The casing comprises a memory to store collected patient data.

The casing further comprises a plurality of electrodes that includes a first ECG electrode, a second ECG electrode, and a third electrode. The first ECG electrode is placed on an outer surface of the casing. The second ECG electrode and the third electrode are placed on each side of the casing to facilitate a thumb and fingers of a user to be placed on the electrodes. The electrodes are configured to capture data indicative of the VTE risk of the user.

The user is guided through instruction from a HED where to place the device on their body.

In another embodiment, the computing device identifies unique physiological markers of the user comprising previously collected sensor data.

In another embodiment, the data indicating a high probability of VTE triggers a message transmission to a healthcare professional.

An aspect of the present disclosure relates to a vein thromboembolism (VTE) risk assessment system for use with a handheld electronic device (HED). The VTE risk assessment system includes a casing, a plurality of electrodes, and a circuit board. The casing has a shape adapted to secure the HED with the casing. The electrodes include a first ECG electrode, a second ECG electrode, and a third electrode. The first ECG electrode is placed on an outer surface of the casing. The second ECG electrode and the third electrode are placed on each side of the casing to facilitate a thumb and fingers of a user to be placed on the casing having the shape that is adapted to secure the HED. The electrodes are configured to capture data indicative of the VTE risk of the user. The circuit board is configured within the casing and electrically connected with the plurality of electrodes. The circuit board includes a microphonic sensor, a diaphragm, a Photoplethysmography (PPG) sensor, an Inertial Measurement Unit (IMU) sensor, and a microcontroller. The microphonic sensor captures VTE audio signals indicative of the VTE risk of the user. The diaphragm enhances auscultation signals. The Photoplethysmography (PPG) sensor measures blood volume changes in a skin area in response to venous hemodynamic changes in a lower limb. The Inertial Measurement Unit (IMU) sensor captures seismic and auscultation signals indicative of the VTE risk of the user. The IMU sensor includes an IMU sensor signal-enhancing material to amplify seismic and auscultation signals. The microcontroller transmits VTE risk data received from the plurality of electrodes, the microphonic sensor, the PPG sensor, and the IMU sensor to at least one of the HED and a computing device. The computing device is configured to: receive, in one or more temporal windows, a representation of one or more of the IMU sensor, the plurality of electrodes, the PPG sensor, and the microphonic sensor signal recorded by the casing; detect features of the IMU sensor, the PPG sensor, and the microphonic sensor from at least one or more portions of the received representations falling within each of the one or more temporal windows; identify patterns of the features of respective sensors from within the one or more portions based on at least a classification model or a regression model; and calculate, basis the identified patterns, a probability of whether the one or more portions corresponds to a problem with the VTE of the user.

In yet another embodiment, the HED secured with the casing comprises a display screen to display VTE diagnostic information derived from the VTE risk data received from the microcontroller. In many embodiments, the HED can be secured with the casing as well as within the casing and secured with the casing encompasses secured within the casing.

In another embodiment, the casing includes a lens configured to envelop a camera of the HED.

In another embodiment, the lens is configured to block external light when the HED shines a light onto the skin of the user that is used to record one or more images thereof. The one or more images are analyzed based on machine learning for providing insights into the VTE risk of the user.

In another embodiment, the casing includes additional seismic and microphonic sensors, to facilitate the identification of common ambient environmental noise unrelated to the patient's VTE health.

In another embodiment, the data indicating a high probability of VTE triggers a message transmission to a healthcare professional.

In another embodiment, the user is guided through instruction from a HED where to place the device on their body.

In another embodiment, the computing device identifies unique physiological markers of the user comprising previously collected sensor data.

In another embodiment, the casing may be bent and/or curved to ensure better fit and/or contact with the patient's body.

In another embodiment, the casing may be personalized according to measurements of the patient's body.

In another embodiment, the casing may be attached to a strap enabling the casing to be strapped around one or more body parts. This may enable the casing to be tightened as needed and ensure better fit and/or contact with the patient's body. The strap may include a hole adapted to the shape of the casing. Types of straps may include but is not limited to thigh straps, thoracic corsets and/or chest straps.

In another embodiment, the casing is used in conjunction with a thin removable layer to cover the patient facing side of the casing. Such a layer may be used to reduce contamination by covering all flat surfaces of the casing and may be easily removed between different patient uses.

In another embodiment, the casing may consist of microtopographic patterned surfaces. Such patterned surfaces may be designed to have anti-bacterial properties to avoid the accumulation of bacteria on the surfaces.

In another embodiment, the HED may be equipped with one or more of said sensors mentioned herein to enable VTE risk assessment.

In another embodiment, a sensor-equipped HED may further be constructed with an adaptable, stretchable and/or flexible material which may enable the HED to easily bend and adapt to different patient bodies and improve contact with said sensors.

In another embodiment, the processor is automatically configured to identify whether the device has been placed on the right or the left leg, through the use of IMU sensor data.

In another embodiment, the processor is automatically configured to identify where on the user's body the casing has been placed.

In another embodiment, the mobile application may prompt the user to take a photo of their face. This may be beneficial in adjusting for differences in skin colour between individuals during the data collection phase from the one or more PPG sensors within the casing.

In another embodiment, the mobile application may be configured to present a questionnaire to the user. Said questionnaire may include but is not limited to questions pertaining to the health of the user.

In another embodiment, while recording using the casing as described herein, the user may be prompted by the mobile application to make a low, continuous and/or droning sound which may aid in that user's pulmonary embolism assessment.

Other embodiments and advantages will become readily apparent to those skilled in the art upon viewing the drawings and reading the detailed description hereafter, all without departing from the spirit and the scope of the invention. The drawings and detailed descriptions presented herein are to be regarded as illustrative in nature and not in any way as restrictive.

Other features of embodiments of the present disclosure will be apparent from accompanying drawings and from the detailed description that follows.

BRIEF DESCRIPTION OF THE DRAWINGS

In the figures, similar components and similar features may have the same reference labels. Further, various components of the same type may be distinguished by following the reference label with a second label that distinguishes among the similar components. If only the first reference label is used in the specification, the description applies to any one of the similar components having the same first reference label irrespective of the second reference label.

FIGS. 9a-9c illustrate a plurality of user interfaces to depict a plurality of operations performed by the mobile application in accordance with at least one embodiment of the claimed subject matter;

DETAILED DESCRIPTION

The present disclosure is best understood with reference to the detailed figures and description set forth herein. Various embodiments of the present systems and methods have been discussed with reference to the figures. However, those skilled in the art will readily appreciate that the detailed description provided herein including the figures are presented for explanatory purposes and the embodiments extend beyond the currently described embodiments. For instance, the teachings and results presented in any particular described application may yield multiple alternative approaches and may be implemented in any suitable manner.

The described embodiments may be implemented manually, automatically, and any combination thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the present embodiments pertains. Persons skilled in the art will envision many other possible variations that are within the scope of the claimed subject matter.

Figure 1:
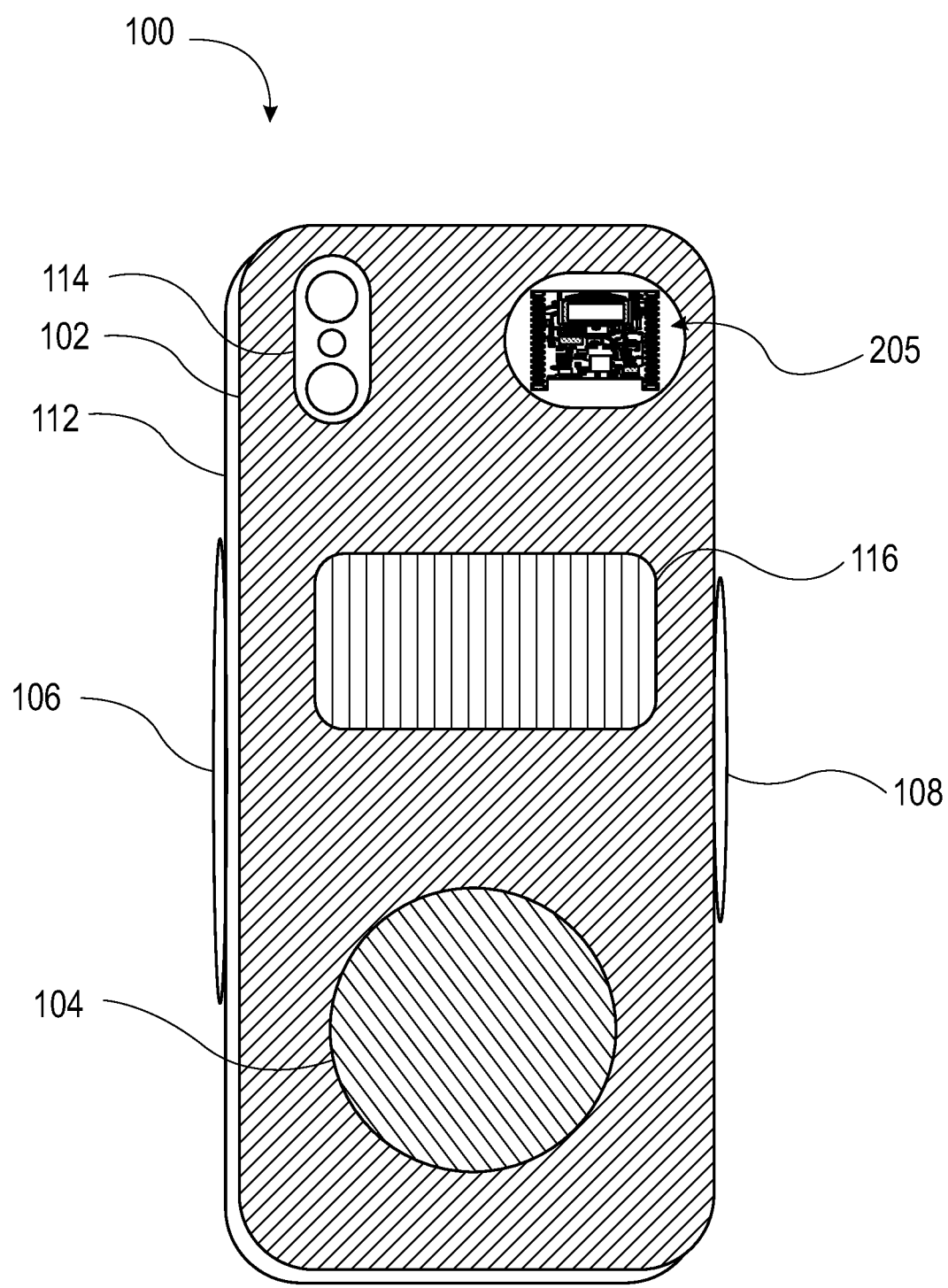
FIG. 1 illustrates a perspective view of the various components of the present vein thromboembolism (VTE) risk assessment system for use with a handheld electronic device (HED) in accordance with at least one embodiment of the claimed subject matter.
Figure 2:
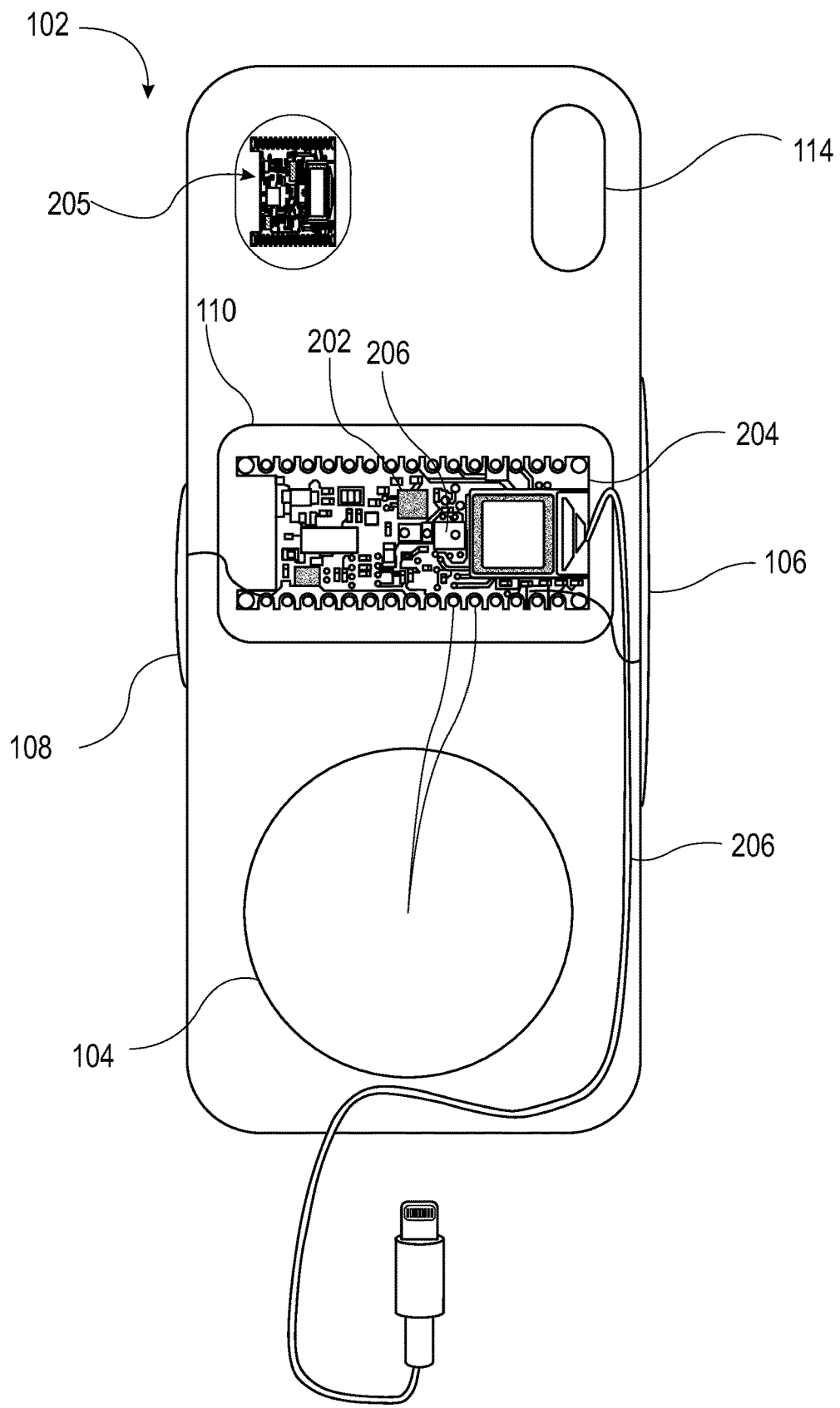
FIG. 2 illustrates an exploded view of the various components of the casing in accordance with at least one embodiments of the claimed subject matter.

FIG. 1 illustrates a perspective view of an embodiment 100 which includes various components for use with a handheld electronic device (HED) 112. Embodiment 100 includes a casing 102 having a shape adapted to secure the HED 112 that can be positioned with or within at least a portion of the casing 102. In many embodiments, the positioning of the HED 112 with the casing 102 may encompass or include the positioning of the HED 112 within all or a portion of the casing 102. In many embodiments, the shape of the casing 102 can be adapted for any suitable HED 112, for example a mobile phone or smartphone. In many of the embodiments, the HED 112 can be accommodated and positioned securely within all or a portion of the casing 102. In these embodiments, the casing 102 includes a plurality of electrodes 104, 106, and 108, and a circuit board 110. The shape of the casing 102 can be adapted for the HED 112, for example a mobile phone or a smartphone, so that the HED 112 can fit and be secured into the casing 102. As shown in FIG. 2, the plurality of electrodes include a first ECG electrode 104, a second ECG electrode 106, and a third ECG electrode 108. The first ECG electrode 104 is placed on an outer surface of the casing 102. The second ECG electrode 106 and the third ECG electrode 108 are placed on each side of the casing 102 to facilitate a thumb and fingers of a user to be placed on the casing 102 (at the same time with the casing 102 having a shape that is adapted to secure the HED 112.) In these embodiments, the ECG electrodes 104, 106, and 108 are configured to capture data indicative of the VTE risk of the user.

FIG. 2 illustrates an exploded view of the various components of the casing 102 in accordance with embodiments of the claimed subject matter and can be viewed in conjunction with FIG. 1. As shown in FIG. 2, the circuit board 110, configured within the casing 102 is electrically connected with the plurality of ECG electrodes 104, 106, and 108. In these embodiments, the circuit board 110 includes a microphonic sensor 202, a diaphragm 204, a Photoplethysmography (PPG) sensor 205, an Inertial Measurement Unit (IMU) sensor 206, and a microcontroller (not shown). The microphonic sensor 202 captures VTE audio signals indicative of the VTE risk of the user. The diaphragm 204 enhances the auscultation signals. In many embodiments, the diaphragm 204 includes an enhancer unit such as a bell-like object to amplify low-frequency auscultation signals pertaining to the VTE audio signals. The bell-like object may be any suitable enhancing element known to those skilled in the art. In some embodiments, the diaphragm 204 may be configured as a tube structure to enhance low-frequency sounds although the tube structure may be configured in any other suitable form such as in a stethoscope type configuration.

In many of these embodiments, the PPG sensor 205 measures blood volume changes in a skin area in response to venous hemodynamic changes in a lower limb. In other embodiments, an upper limb may be monitored and in other embodiments multiple limbs may be monitored at the same time. In many of the embodiments, the PPG sensor 205 generates infrared (IR) light to measure the blood volume in a lower limb. In these embodiments, the PPG sensor 205 is a non-invasive, inexpensive, and convenient diagnostic tool to measure oxygen saturation, blood pressure, and cardiac output. In many embodiments, the PPG sensor 205 is placed at the top right of the casing 102 and may be connected to one or more additional microcontrollers.

Embodiments also include an Inertial Measurement Unit sensor 206 for capturing seismic and auscultation signals that are indicative of the VTE risk of the user. The IMU sensor 206 includes an IMU sensor signal enhancing material 116 that amplifies seismic and auscultation signals. Examples of the IMU sensor signal enhancing material include but are not limited to: sound absorbers made from porous materials, micro-perforated plates, and micro-perforated panel absorbers backed with mechanical impedance plates where the backed cavity is limited as well as combinations thereof. Other signal enhancing materials known to those skilled in the art may also be used instead or in conjunction with one or more of the aforementioned materials. The microcontroller transmits VTE risk data received from the plurality of ECG electrodes 104, 106, and 108, the microphonic sensor 202, the PPG sensor 205, and the IMU sensor 206 to the HED 112 and a computing device such as the server 306 illustrated in FIG. 3.

In many embodiments, the casing 102 includes a lens 114 configured to envelop the camera of the HED 112. The lens 114 may be configured to cover all or a portion of the camera of the HED 112. In some of these embodiments, the lens is configured to block all or a portion of the external light shined into the skin of the patient while the embodiment is simultaneously capturing images or video of the skin and the associated features of the skin. In some embodiments, video in additional to or instead of one or more images may be recorded by the camera.

In these embodiments, the camera is used to record one or more images (or video) of the user's skin area and the one or more images (or video) are analyzed by the system using machine learning which aids in providing insights into the VTE risk of the user based on differences in the detected tissue colors. Utilizing machine learning, for example applying one or more image recognition machine learning models to one or more recorded images, helps in providing insights into assessing the VTE risk. In many embodiments, the HED 112 includes a display screen to display VTE diagnostic information derived from the VTE risk data received from the microcontroller.

In several embodiments, the casing 102 includes additional seismic and microphonic sensors to facilitate the identification of common ambient environmental noise unrelated to the patient's VTE health. In several embodiments, the data indicating a high probability of VTE triggers a message transmission to a healthcare professional. In an embodiment, the user is guided through instruction from a HED 112 relating to where to place the device on their body. In an embodiment, the computing device identifies unique physiological markers of the user based on previously collected sensor data.

In some embodiments, the casing 102 includes one or more speakers and/or transducers, which can be configured to send out sound waves into the body of the patient which can also be the user so that the reflection of the sound waves can be used to identify physiological processes that may be occurring at one or more sound frequencies or ranges of sound frequencies.

In an embodiment, the casing 102 includes a battery configured to supply electrical power to the circuit board 110, wherein the battery may receive power from one or more external source at different times or at a constant power level. In these embodiments, the casing 102 connects to the HED 112 using a power cable 206. In some embodiments, the casing 102 includes a plurality of additional seismic and microphonic sensors to facilitate the identification of common ambient environmental noise unrelated to the patient's VTE risk. In many of these embodiments, the presence of data indicating a high severity of a VTE risk triggers the transmission of one or more messages to a healthcare professional or another health monitor system or individual.

In many embodiments, the user is guided by the HED 112 through instructions, for example visual, tactile or audio instructions, as to where to place the device on the user's body. In some embodiments, the instructions may indicate corrective actions the user can take to optimally place the HED 112 on the user's body. In many embodiments, the VTE risk assessment system identifies unique physiological markers of the user comprising previously collected sensor. Additionally, in many embodiments, previously collected sensor data is used to identify a user's unique physiological markers so that the user is identified as a previous or known user. This information can be used for tracking, monitoring or for further analysis and recommendation of future tests and treatment.

Figure 3:
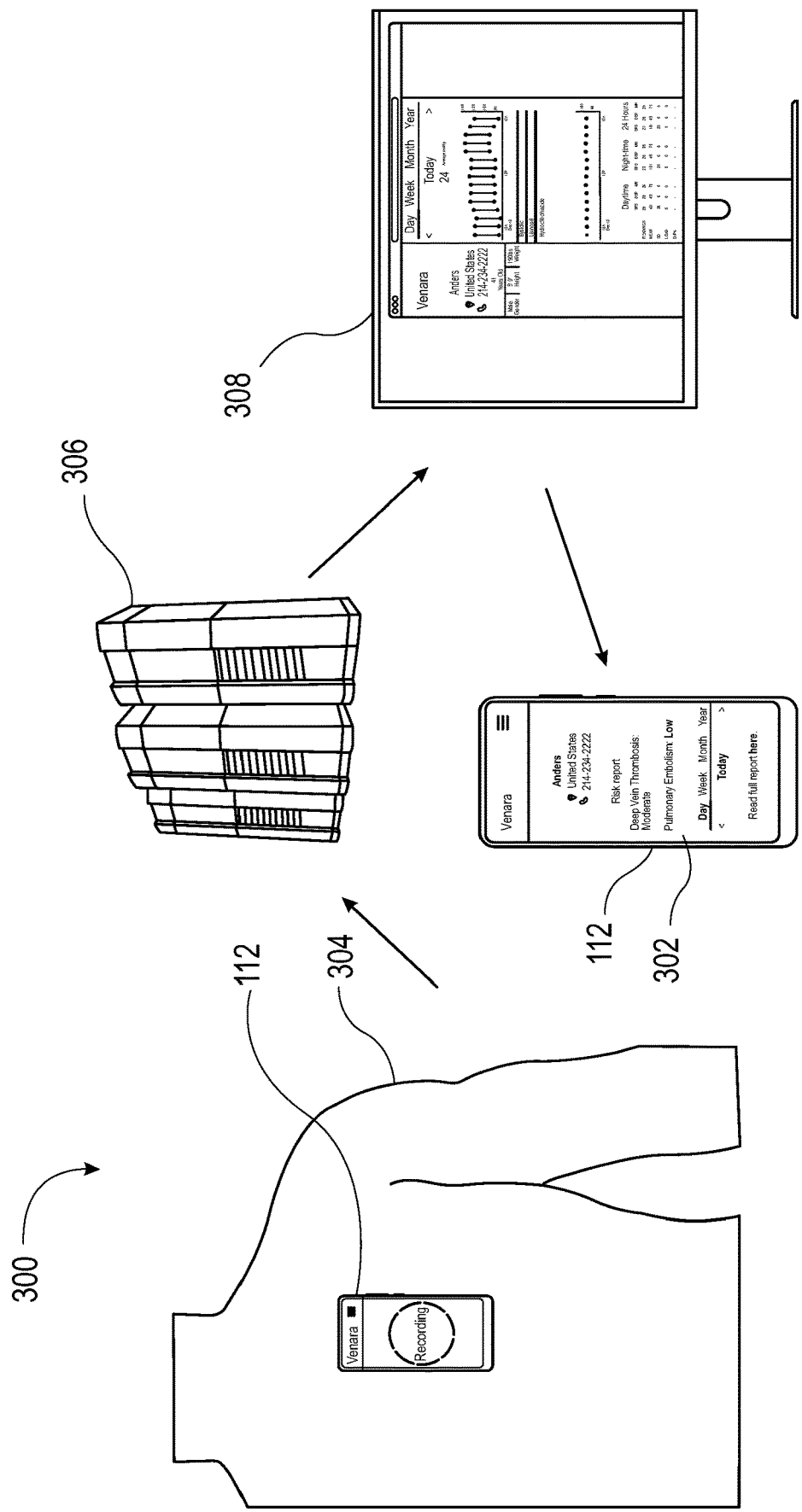
FIG. 3 illustrates a network implementation of the vein thromboembolism (VTE) risk assessment system in accordance with at least one embodiment of the claimed subject matter.

FIG. 3 illustrates a network implementation of the present VTE risk assessment system 300 in accordance with embodiments of the claimed subject matter. In an embodiment, the HED 112 includes a display screen 302 for displaying VTE diagnostic information derived from the VTE risk data received from the microcontroller. In several embodiments, the casing 102 is configured with the HE 112 so it can be positioned against the chest of the user 304 to capture VTE risk data. Further, the casing 102 is configured to capture the VTE risk data of the user when the casing 102 is positioned against the back of the user or against the thoracic cage of the user.

In some embodiments, the HED 112 is positioned and secured within the casing 102 and the HED 112 includes a processor to execute a plurality of instructions pertaining to a VTE risk monitoring application. The processor is configured to display or otherwise communicate one or more commands so that the user can be instructed to position the casing against the chest of the user. The processor further instructs the user (for example, the patient) to hold the casing by the user against his/her chest using a hand.

In many embodiments, the classification model is trained to detect unhealthy VTE. The classification model is trained based on the detected features of the IMU sensor. According to an embodiment herein, the computing device 306 is configured to receive, in one or more temporal windows, a representation of one or more of the following: an IMU sensor, an PPG sensor, and a microphonic sensor signal recorded by the casing. The computing device 306 is configured to detect features of the IMU sensor, the PPG sensor, and the microphonic sensor from at least one or more portions of the received representations falling within each of the one or more temporal windows. The computing device 306 is configured to identify patterns of the features of respective sensors from within the one or more portions based on at least a classification model or a regression model. The computing device 306 is configured to calculate, basis the identified patterns, a probability of whether one or more portions corresponds to the VTE of the user.

In an embodiment, the processor is configured to transmit the data indicative of VTE risk from the HED 112 to a server 306 over a network; and store the data in the server 306 for subsequent analysis by a clinician. Examples of the network could be a combination of a local area network and a wide area network, such as the Internet, through a physical or a wireless connection, for example, a Bluetooth® connection. The network may furthermore be comprised of GSM, 3G, 4G, and/or 5G networks. In an embodiment, the processor is configured to transmit the data indicative of VTE function from the HED 112 to a clinician computing device 308 via the internet for remote diagnostic analysis using machine learning. In an embodiment, the clinician computing device 308 performs risk analysis in the mobile application of the HED 112 and conveys the results in a suitable/presentable format. In an embodiment, the classification model is trained to detect VTE risk. In an embodiment, the microcontroller utilizes a de-noising algorithm, for example using a machine learning library such as TensorFlow Lite.

Figure 4:
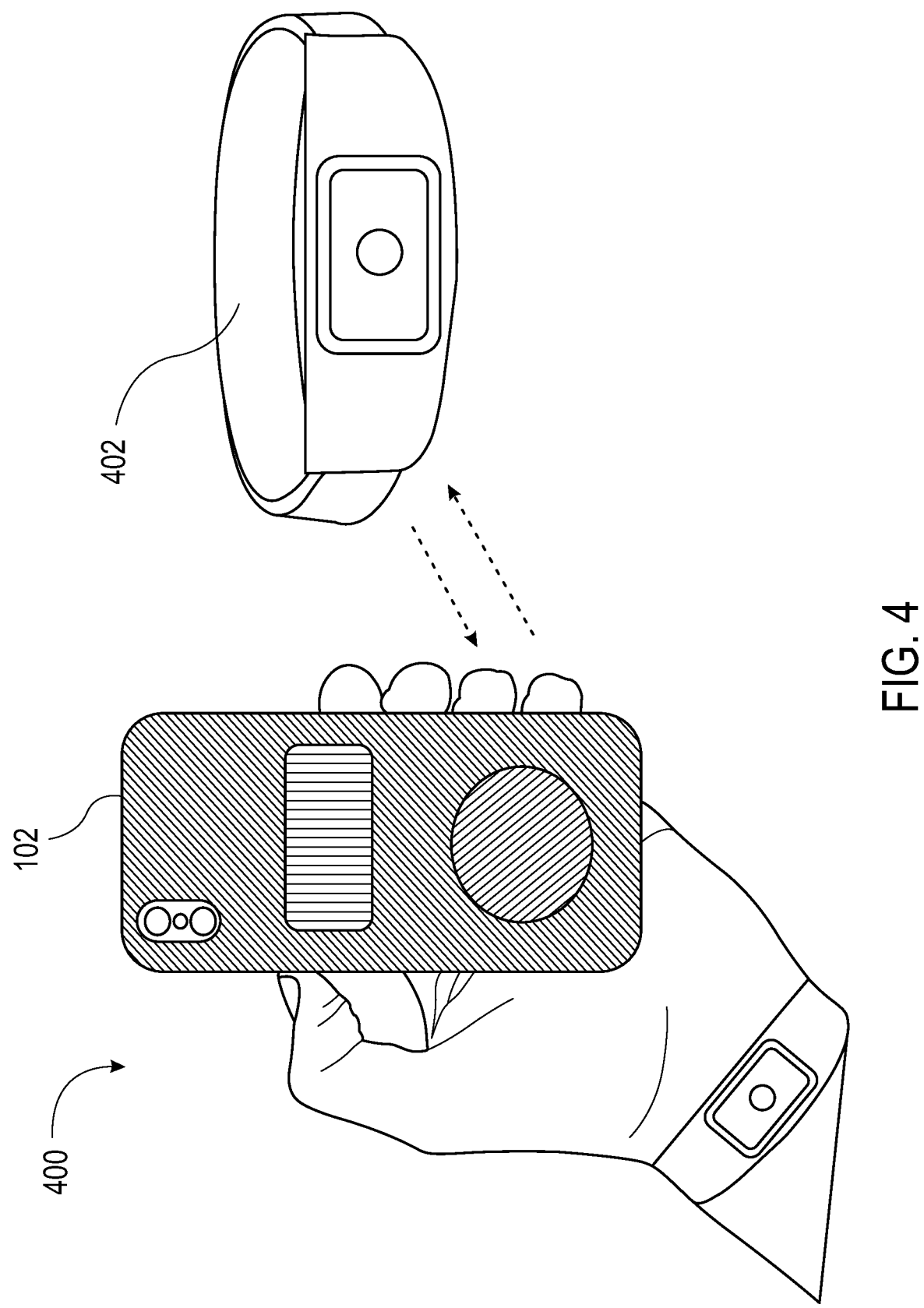
FIG. 4 illustrates a perspective view of communication between the casing and a second handheld electronic device in accordance with at least one embodiment of the claimed subject matter.

FIG. 4 illustrates a perspective view 400 of communication between the casing 102 and a second handheld electronic device 402, in accordance with at least one embodiment. In one embodiment, the VTE risk assessment system includes a second handheld electronic device 402 that includes sensors to collect patient health data and which is worn by the user on the user's wrist and/or calf and is wirelessly connected with the system. Further, the VTE risk assessment system includes a wireless transceiver to establish a communication with the computing device to transmit VTE risk data therebetween. The application is programmable on the HED 112 to transmit diagnostic information derived from VTE risk data received by the wireless transceiver. In an embodiment, the second handheld electronic device 402 is a wearable device which can connect and communicate wirelessly with the HED 112. Examples of the second handheld electronic device 402 include smartphones, smartwatches, PCs, tablets, or any other wearable or handheld device. The HED 112 is able to simultaneously download and examines sensed data in real-time from the second handheld electronic device 402. It is able to process and analyze previously sensed data from one or more different temporal segments that have been saved in the memory of the second handheld electronic device.

In these embodiments, the second handheld electronic device 402 may separate IMU sensor data into segments and subsequently analyze each section to determine if the data indicates that the patient was experiencing VTE at the time the segment was recorded. A classification model can be implemented using a convolutional neural network and/or any other variations of artificial neural network utilization, for example a one-dimensional formulation utilizing the IMU sensor data.

Figure 5:
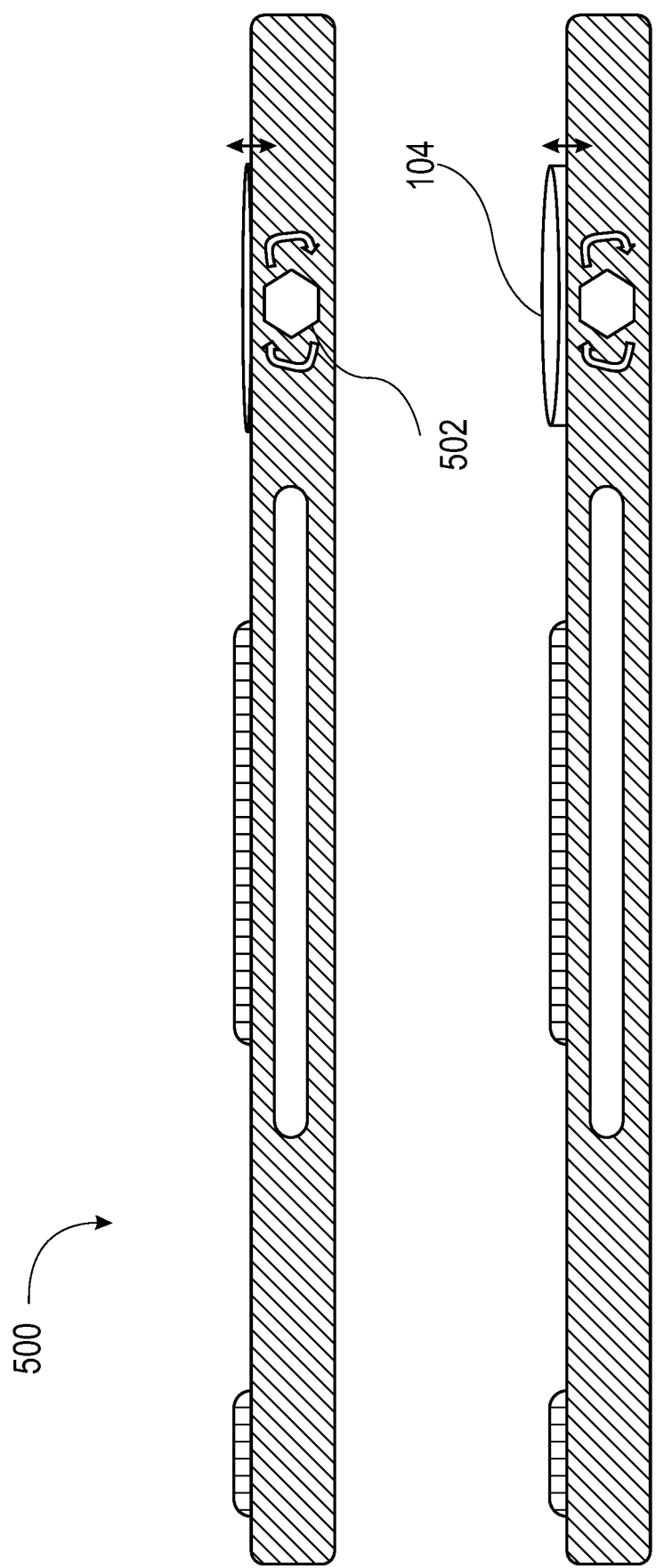
FIG. 5 illustrates a side view of the casing in accordance with at least one embodiment of the claimed subject matter.

FIG. 5 illustrates a side view 500 of the casing 102 in accordance with embodiments of the claimed subject matter. According to one embodiment, the casing 102 includes a button 502 such as a toggle to initiate the operation (e.g. to initiate the in/out data acquisition cycle) of the first ECG electrode 104. Embodiments of the VTE risk assessment system include various sensors employing different technologies allowing for robustness across different recording environments and patient cohorts. In one exemplary embodiment used in a noisy environment, a model such as a classification model and/or a regression model may be trained to emphasize visual or seismic sensors. In another exemplary embodiment used with a patient having darker skin wherein light is less able to penetrate the user's skin, a model such as a classification model and/or a regression model may be trained to emphasize sensors pertaining to audio and/or electrophysiological sensors. In many embodiments, the processor is configured to provide instructions pertaining to the management of the user's medical condition. Also, in many embodiments, the casing 102 also includes an ultrasound transducer, a magnet, radiofrequency coils, and a gradient coil.

According to many embodiments, the VTE risk assessment provides an ability to operate the casing 102, without a battery directly connected to the casing 102, instead using power from an exterior electronic device's power source. Embodiments having these configurations allow for more space and therefore larger and more powerful sensors may be used to further enhance data collection quality and accuracy. The absence of an internal or external battery connected to the casing 102 may also reduce the amount of electrical interference inherent to the sensors communicating with the casing 102. This can allow for a more powerful device and obviate the necessity of having multiple VTE risk assessment devices for identifying different lung conditions. With the use of a single device that can accurately analyze a number of lung conditions instead of just a few, the patient experience is substantially improved potentially increasing the patient's ease and willingness to undertake regular monitoring.

The utilization of a handheld electronic device with the casing can improve the accuracy of the casing 102's readings in a number of ways. For example, using the electronic device's internal accelerometer and microphonic sensors external data noise pertaining to both movement and sound can be measured with the resulting measurements aiding in the process of removing noise from the data so that the analysis can be made on data most relevant to VTE health conditions. The internal accelerometer and microphonic sensor can act as a sensors to provides an acoustic signal and other information that convey data associated with internal respiratory sounds. In some embodiments, the acoustic sensor senses tissue vibration and conveys information relating to the movement of tissues.

Embodiments using smartphones allow users a simplified means to monitor their health using a familiar device. The user can carry the embodiments throughout their day and night and the casing 102 can also function as a protective barrier against breakage, surface scratching, and damaging environmental hazards such as water. Another benefit of the self-health monitoring embodiments is the use of a single device instead of multiple devices which can reduce the likelihood of misplacing a single device versus keeping track of multiple devices. The embodiments also allow the use of battery power instead of or in addition to dedicated power from wired outlets allowing users to charge the embodiments at their convenience such as at regular times during the day or night. Another benefit of the embodiments is the ability of a user to record data at standardized time intervals.

In use, many of the embodiments allow a patient may use one or more internal alarm clocks for reminders as well as prompt the user to perform data recording functions. In many embodiments, the user can take readings at approximately the same time each day (and/or at a same location or position) to allow the data collection to be performed during similar recording environments leading to a more standardized data collection further aiding in the reduction of noise in the collected data.

Figure 6A:
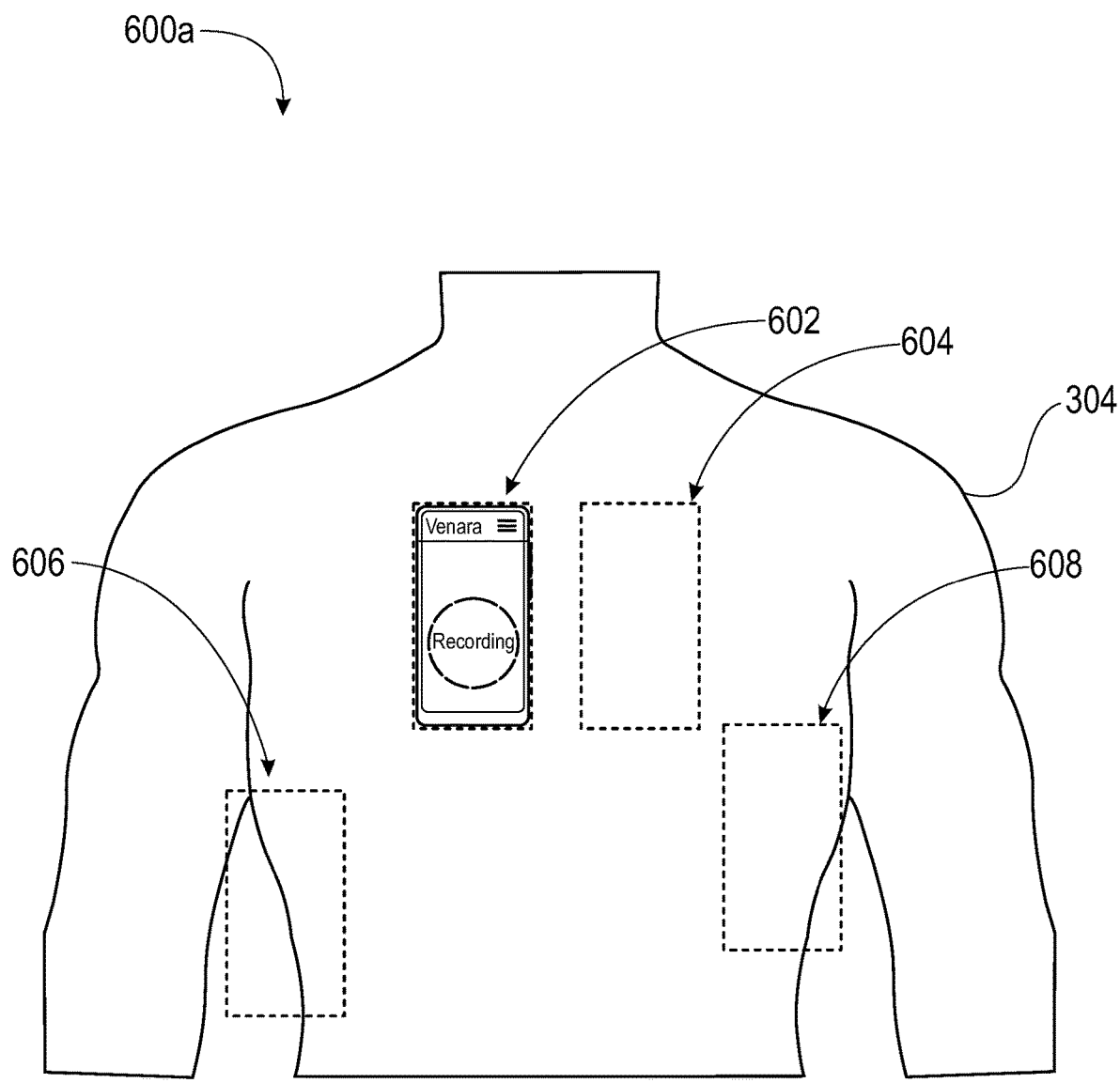
FIG. 6a illustrates a perspective view of the placement of the casing on the patient's chest and rib cage in accordance with at least one embodiment of the claimed subject matter.
Figure 6B:
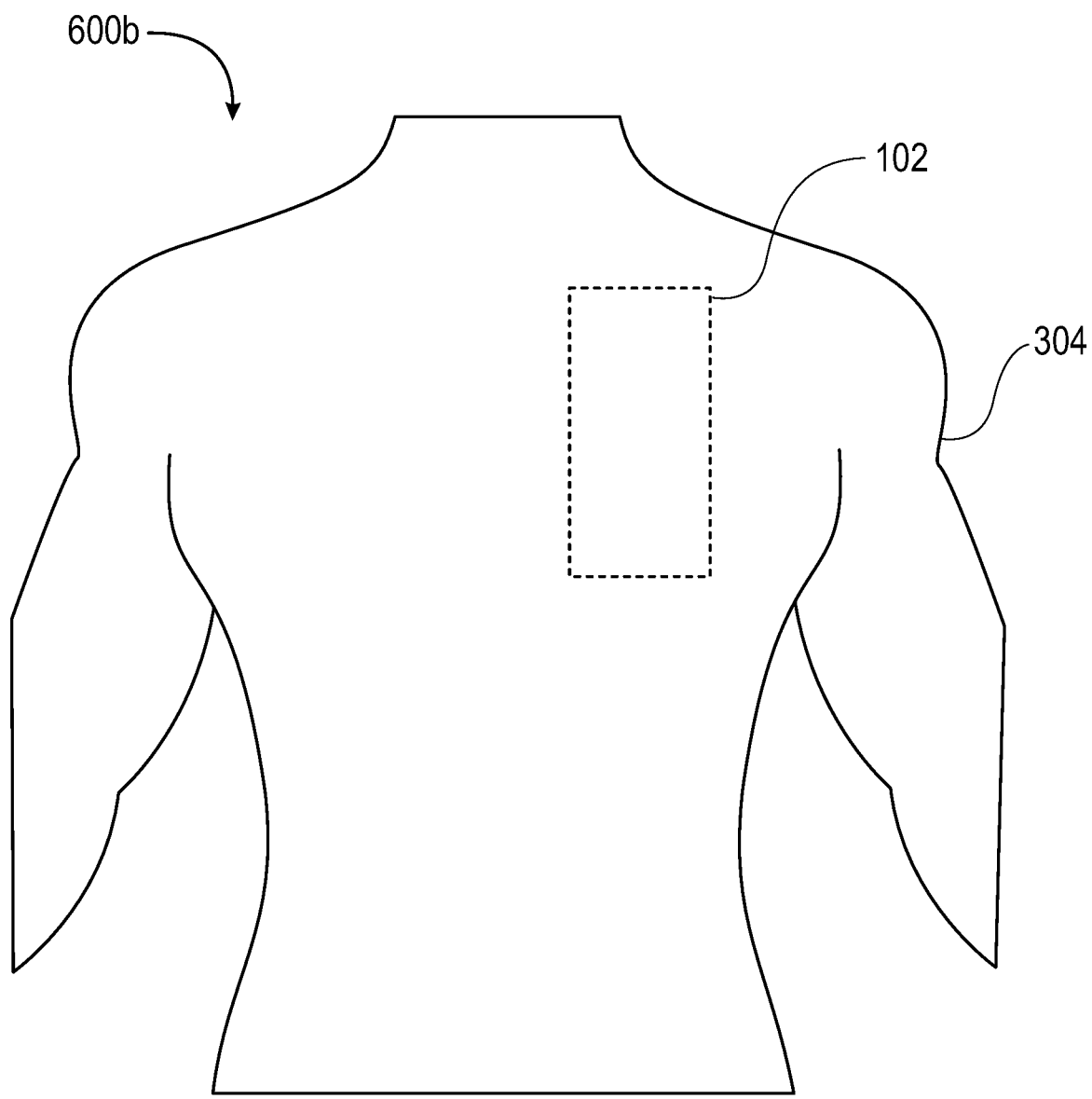
FIG. 6b illustrates a perspective view of the placement of the casing on the back portion of the patient's body in accordance with at least one embodiment of the claimed subject matter.

FIG. 6a illustrates a perspective view 600a of the placement of the casing 102 on the patient's chest and rib cage in accordance with many embodiments. FIG. 6a is explained in conjunction with FIG. 1. As shown in FIG. 6a, the casing 102 is placed centrally on the patient's chest. In some embodiments, the software application executed on the mobile phone (or a remote server) may be used to direct the user 304 to position or correct the placement of the casing 102 on the chest of the user 304 or, in other instances, the body of another person. Audio, visual, or tactile instructions or any directions originating from the embodiment may include a first step 602 of placing the casing 102 in a position about a finger length's distance below the patient's right collarbone, alongside the sternum, and then, in a second step 604, placing the casing 102 in a position about a finger length's distance below the patient's left collarbone alongside the sternum. Next, in a third step 606, the user is instructed to place the casing 102 at the right rib cage of the patient, and in a fourth step 608, the user is instructed to place the casing on the outer surface at the left rib cage of the patient so that steps 602 through 608 allow the embodiments to capture the user's VTE risk data. FIG. 6b illustrates a perspective view 600b of the placement of the casing 102 on the back portion of the user's 304 body, in accordance with at least one embodiment. In this position against the back of the user 304, the embodiment can capture VTE risk data of the user 304.

Figure 7:
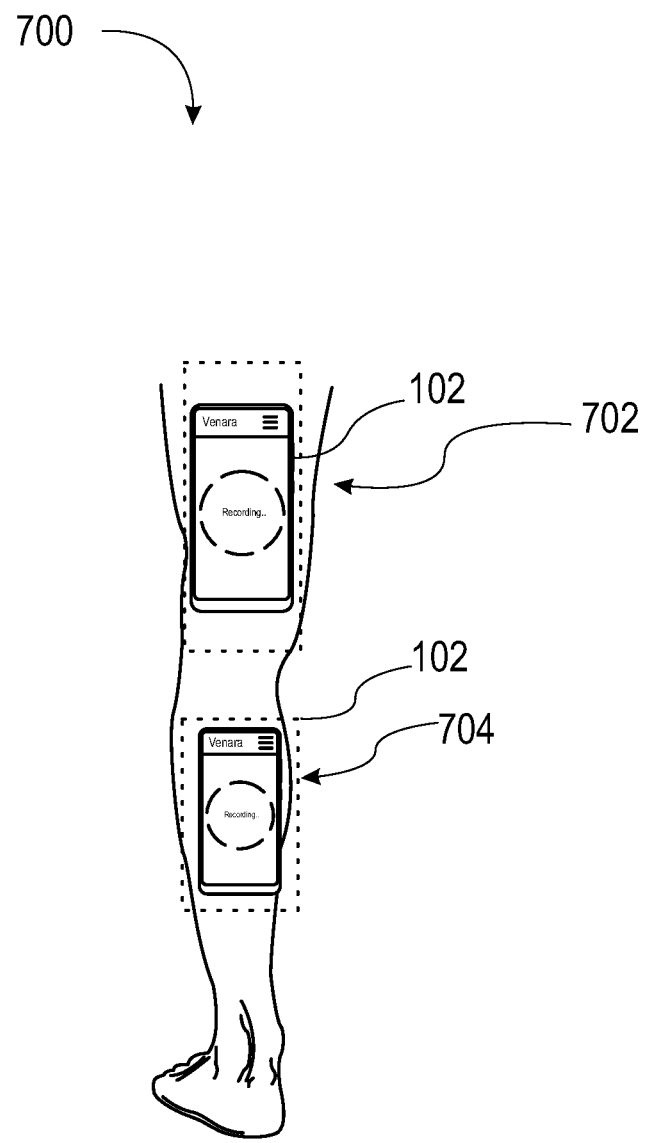
FIG. 7 illustrates a perspective view of the placement of the casing on the lower limb of the patient in accordance with at least one embodiment of the claimed subject matter.

FIG. 7 illustrates a perspective view 700 of the placement of the casing 102 on the lower limb of the patient, in accordance with at least one embodiment. The casing 102 is placed on the patient's lower limb to capture the VTE risk data. In some embodiments, the software application executed on the mobile phone may be used to direct the user to correct placement of the casing 102 on their thigh.

Embodiments include a first step 702 instructing the user to place the casing 102 on the patient's thigh, and then a second step 704 for placing the casing 102 on the calf of the patient to capture VTE risk data. In these embodiments, the patient maintains recording/capturing VTE risk data until the application instructs the user to stop maintaining the embodiment in its position. Once the user is instructed to do so, the user presses a stop button (which is displayed on the application) and the VTE risk data is uploaded to the server. In other embodiments, the user does not have to press a button to stop the data acquisition process. In an embodiment, the computing device identifies unique physiological markers of the user using previously collected and stored sensor data. In an embodiment, the data indicating a high probability of VTE triggers a message transmission to a healthcare professional. According to some embodiments, the casing 102 is used as a patch with the ability to adhere to the patient's body. The patch can also be placed on the side of the user's leg or any other suitable position on the user's body. The patch can be held by the user so that ECG measurements can be taken while the patch is positioned on the user. In some embodiments, the patch can be worn as a wearable/patch permanently or semi permanently with the use of an adhesive material or a removably positioned strap.

Figure 8C:
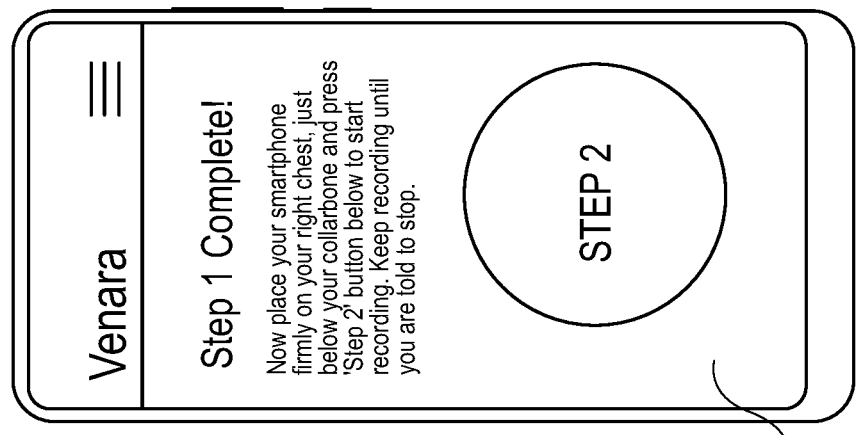
FIGS. 8a-8c illustrate a plurality of user interfaces to depict a plurality of directions pertaining to the usage of the casing in accordance with at least one embodiment of the claimed subject matter.
Figure 8B:
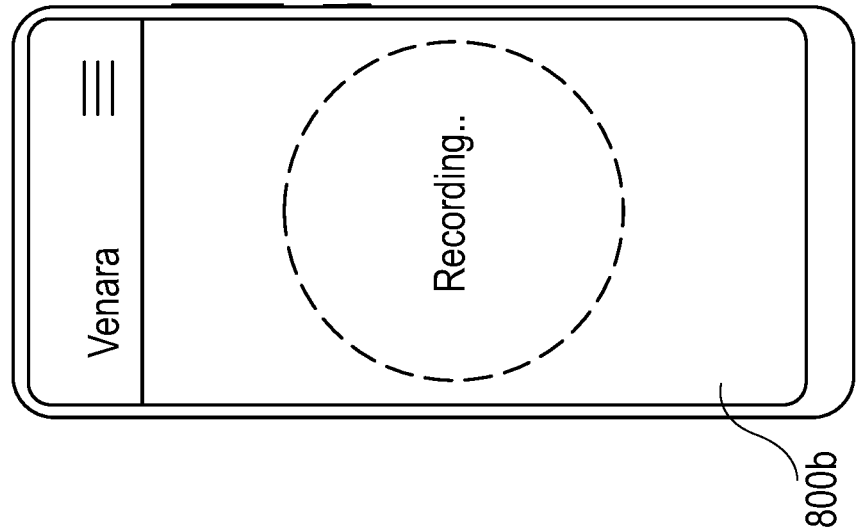
Figure 8A:
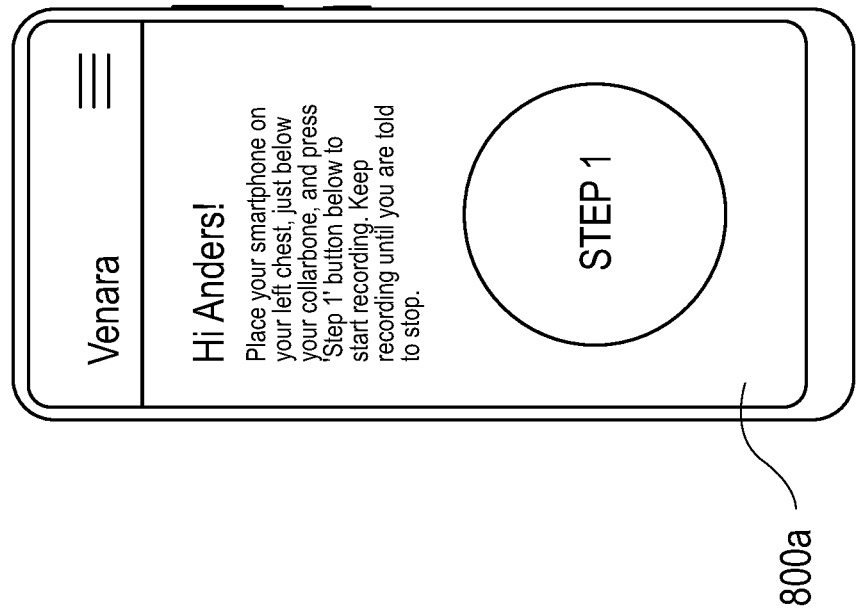

FIGS. 8a-8c illustrate several user interfaces 800a, 800b, and 800c depicting visual directions regarding the usage of the various components of the embodiments. The user interface 800a depicts a exemplary first step shown to the user so that the user is instructed to place the HED 112 approximately a finger's distance below the patient's left collarbone and then to press the 'Step 1' button to initiate recording after which the user is shown the exemplary user interface of 800b. In these embodiments, the user is instructed to maintain the position of the casing 102 until the embodiment communicates that the user can disengage the positioning of the casing 102. After the recording is completed, the user interface 800c depicts "Step 1 complete!" and instructs the user to place the smartphone firmly on his/her right chest, just below the collarbone, and press the 'Step 2' button below to start recording. After the recording has stopped, the software application notifies the user that she or he can stop holding the device in the referenced recording position.

FIGS. 9a-9c illustrate user interfaces 900a, 900b, and 900c to depict a plurality of operations performed by the mobile application, in accordance with many embodiments.

The user interface 900a shows the mobile application directing the user to begin an upload of the VTE risk data received from the plurality of electrodes, the microphonic sensor, and the IMU sensor. The user interface 900b depicts the VTE risk data being uploaded and finishing the upload. The user interface 900c depicts the pending analysis of the VTE risk data to figure out where it is most ideal to place the casing can furthermore help standardize data collection quality across different patient cohorts. In many embodiments, the mobile application is able to recall from stored information certain physical features and/or characteristics associated with the patient's VTE risk signals which may be interpreted as the patient's "VTE risk ID". This feature can help ensure that the data collected can be verified as belonging to the patient and not someone else. It may furthermore indicate when the patient may have placed the casing in the wrong location and prompt the patient to reposition the casing.

In some embodiments, the data collected through the casing may be combined with data from one or more wearable electronic devices. By combining data from one or more other sources, for example a wearable device with sensors positioned on the wrist of a patient, accuracy can be improved leading to a greater ability to calculate pulse transit time and compare data between different parts of the body at the same time. Other data may include data from pulse oximetry readings as well as any other suitable VTE risk indication. In some embodiments, the casing 102 may be equipped with a wireless charging station to allow for wireless charging of other devices such as wearable devices. A wearable device (with or without an internal or external battery) may be connected to the casing 102 and used to simultaneously record data and the device may draw power from the casing 102.

After the data are recorded, they can be analyzed in the connected HED 112 or another connected computing device. For instance, the data may be uploaded to one or more servers where it can be analyzed or communicated to one or more other devices including storage devices. The data may also be analyzed by any combination of computing devices and servers. Embodiments may use any suitable methods for data analysis including, but not limited to, machine learning-based methods that are used to classify whether the data indicates certain lung conditions are present. The machine learning methods used in the embodiments include, but are not limited to one or more of the following methods: decision tree-based machine learning methods, artificial neural networks, convolutional neural networks, logistic regression, naive Bayes, nearest neighbor, support vector machines, boosted tree learning methods, and deep learning methods.

One or more models, for example the classification model and the regression model, may be trained on data that are collected by the various sensors of the embodiments Image-based indications of VTE risk may be used as a marker with a binary outcome of clinical diagnosis based on that picture. Those indications with or without other data may also be used to derive a percentage number indicating the severity of said VTE risk. A clinician's diagnoses can also be used to train the models to improve the accuracy of the models and algorithms.

Figure 10:
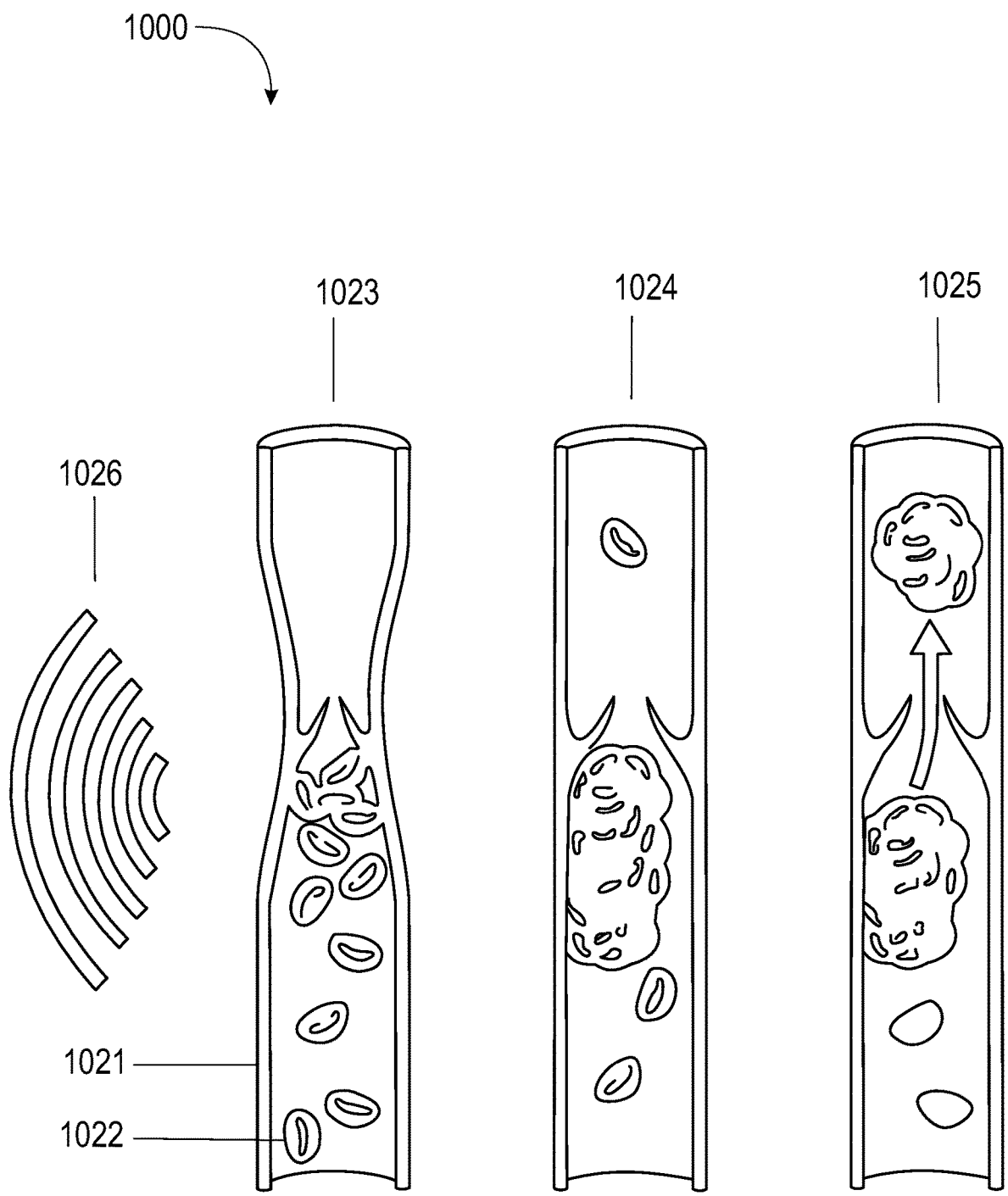
FIG. 10 illustrates a perspective view of the deep vein thrombosis (part of vein thromboembolism (VTE)) in accordance with at least one embodiment of the claimed subject matter.

FIG. 10 shows a perspective view 1000 of examples of deep vein thrombosis (a subset of vein thromboembolism (VTE)) in accordance with at least one embodiment. This view 1000 further shows a representation of VTE with a deep vein thrombosis (DVT) example and a pulmonary embolism example which can provide indications that an IMU sensor may identify and on which it senses and relays data. As the blood 1022 flowing within vein 1021 becomes clotted, a thrombus starts building up and illustration 1023 shows an example of the beginning of this type of DVT. Illustration 1024 shows the continuation of the process of DVT as the thrombus clots and occludes blood flow within the vein. The thrombus may become enlarged and released into the rest of the cardiac system resulting in an embolus 1025. This may result in a pulmonary embolism and is potentially fatal. These illustrated internal venous dynamics provide examples that would lead to indications encompassed in signals 1026 that can derived form a number of sensors, including but not limited to IMU sensors and acoustic sensors.

Figure 11:
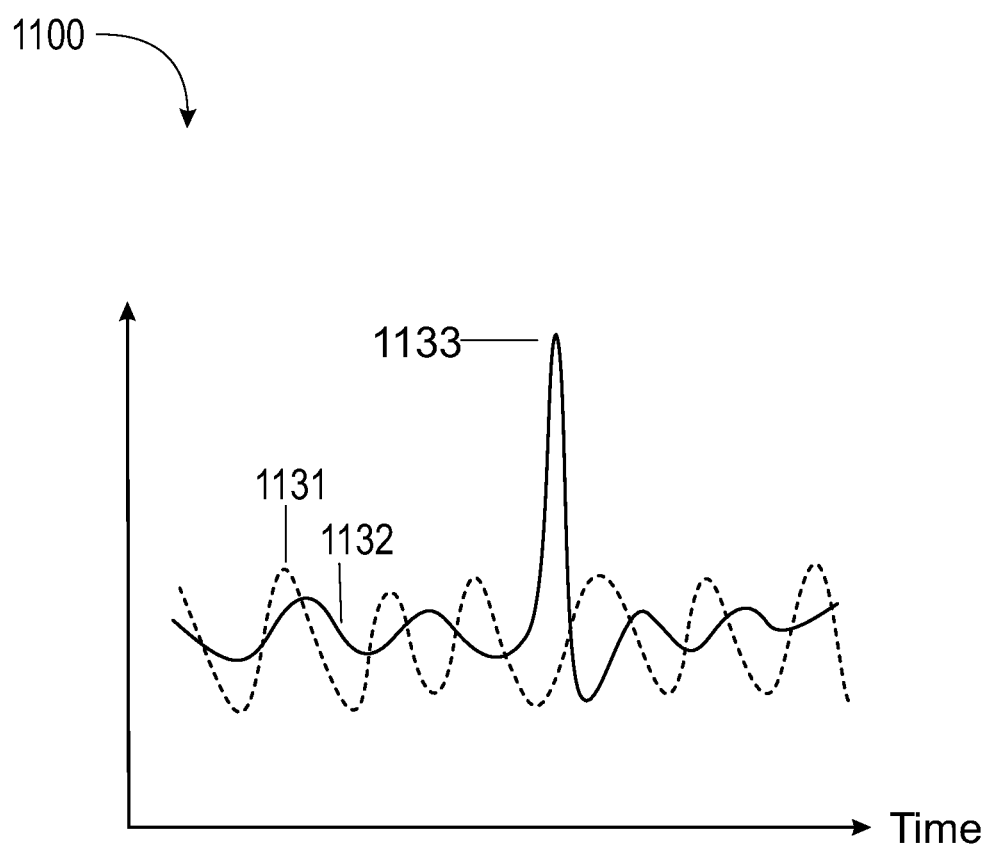
FIG. 11 illustrates a graphical representation of the IMU and/or microphone signal level in accordance with at least one embodiment of the claimed subject matter.

FIG. 11 illustrates a graphical representation 1100 of an IMU data waveform derived from microphone signal levels in accordance with embodiments of the claimed subject matter. As shown, time is represented on the x-axis through units of tenths of a second and IMU signals are represented on the y-axis including but not limited to units of specific force, angular rate, and orientation. When clots build-up and/or are released such as shown in examples 1023, 1024, and 1025, the internal dynamics of the vein changes, and a waveform typically associated with smooth blood flow may temporarily be disrupted 1133. Normal blood flow can be expected to be represented by a more steady and recurring wavelike forms such as waveform 1131. These types of blood flow disruptions may not be easily identifiable so the embodiments may require machine learning methods to aid in the detection of microscopic perturbations and variance in venous blood flow.

These intervals may reveal underlying hemodynamic problems thus representing another reason why unique data points relating to IMU and/or other sensor technology through the extended wear IMU and the physiological sensor monitor described herein can be important for understanding the general health of a patient. The long-term data acquisition of these IMU data points, obtained through extended wear of a wearable monitor can give a patient valuable insights into her or his own hemodynamic function and general physical health.

Figure 12:
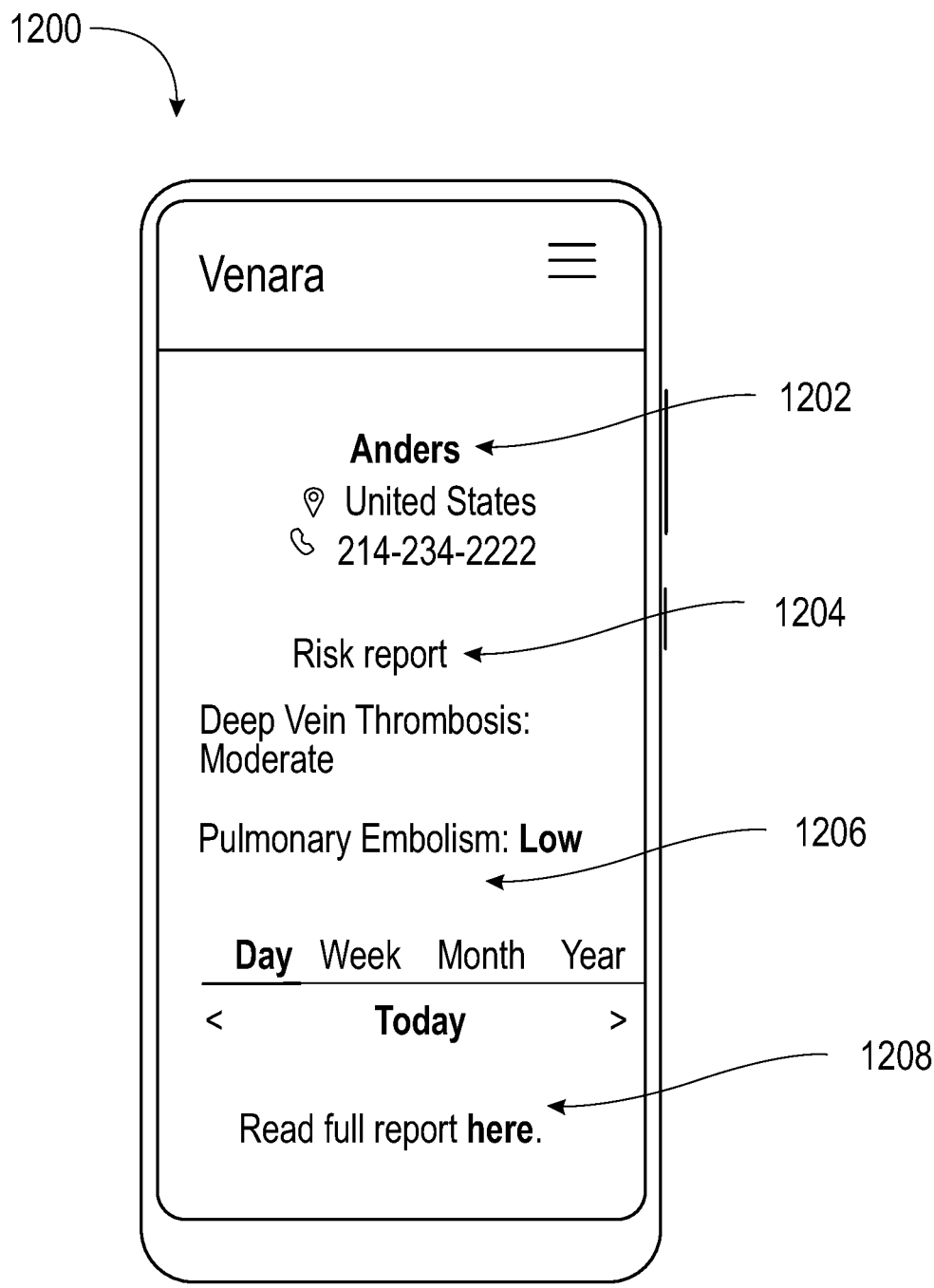
FIG. 12 illustrates a user interface to depict personal information and VTE diagnostic information pertaining to the user in accordance with at least one embodiment of the claimed subject matter.

FIG. 12 illustrates a user interface 1200 depicting personal information and VTE diagnostic information pertaining to the user in accordance with at least one embodiment. The results of the analysis of the user's data are presented through the mobile application as shown in interface 1200 to the patient or to any other person of the patient's choosing. In some embodiments, an email message might be sent to the patient's clinician with a report of the recording. Block 1202 of the user interface 1000 shows a patient name and her or his contact information. Block 1204 show the results from the analysis of the VTE risk data and block 1206 (appearing below block 1204) shows an interface which allows a user to view and compare results with past results. Block 1208 shows an interface which allows a user or anyone else designated by the user to manually review the data from each recording.

Figure 13:
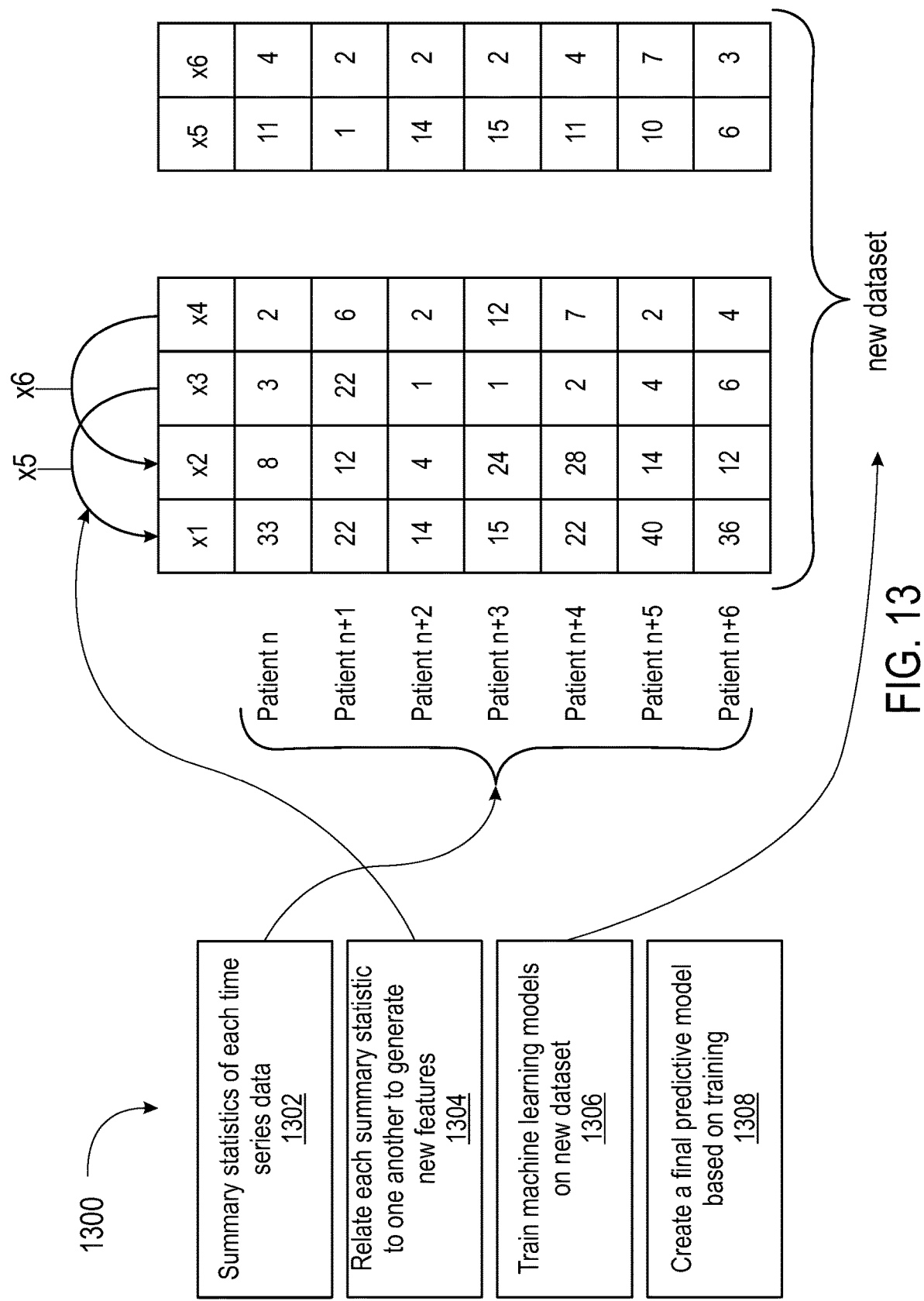
FIG. 13 illustrates a flow diagram of feature generation through a division of columns by one another in accordance with at least one embodiment of the claimed subject matter.

FIG. 13 illustrates a flow diagram 1300 of feature generation through a division of columns by one another in accordance with embodiments of the claimed subject matter. Step 1302 shows a step wherein summary statistics a created using the time series data pertaining to a plurality of the patients. Step 1304 shows a step wherein the flow diagram relates each summary statistic to one another to generate new features. Step 1306 shows a step wherein machine learning models are trained on a new dataset. Step 1308 shows a step wherein a final predictive model is created based on the training of one or more machine learning models.

Unless otherwise defined, all terms (including technical and scientific terms) used in this disclosure have the same meaning as commonly understood by one of ordinary skill in the art to which this disclosure belongs. It is to be understood that the phrases or terms used with the present inventive subject matter are for the purpose of description and not of limitation. As will be appreciated by one of skill in the art, the present disclosure may be embodied as a device, system, and method and/or one or more computer programs. Further, the embodiments may include one or more forms of a computer program product on a computer-readable storage medium having computer-usable program code embodied in the medium. The present systems, devices, and methods have been described above with reference to specific examples, however, other embodiments and examples than the above description are equally possible within the scope of the claimed subject matter. Even though modifications and changes may be suggested by the persons skilled in the art, it is the intention of the inventors to embody all the changes and modifications that may reasonably come within the scope of the contribution the inventors to the art.

What is claimed is:

1. A vein thromboembolism (VTE) risk assessment system, the VTE risk assessment system comprising:
   a handheld electronic device (HEI) with a casing having a shape adapted to secure a plurality of components with said casing comprising:
   a microphonic sensor to capture audio signals from a user's body indicative of a VTE risk of the user;
   a Photoplethysmography (PPG) sensor configured to measure blood volume changes in a skin area in response to venous hemodynamic changes in a lower limb;
   an Inertial Measurement Unit (IMU) sensor to capture seismic signals indicative of the VTE risk of the user;
   a diaphragm to enhance auscultation signals; and
   a microcontroller to transmit data received from the microphonic sensor, the PPG sensor, and the IMU sensor to a computing device, wherein the computing device is configured to:
      receive, in one or more temporal windows, a representation of data from one or more of the following: the IMU sensor, the PPG sensor signals, and the microphonic sensor signals;
      detect features from at least one or more portions of the received representations of data that fall within each of the one or more temporal windows;
      identify patterns in the detected features based on one or more of the following models: a classification model and a regression model; and
      using the identified patterns, calculate, a probability of whether the identified patterns corresponds to the VTE risk of the user.

2. The VTE risk assessment system according to claim 1, further comprising one or more speakers which can be configured to send sound waves into a patient's body which can also be the body of the user so that a reflection of the sound waves can be used to identify physiological processes that may be occurring at one or more sound frequencies.

3. The VTE risk assessment system according to claim 1, wherein the casing is configured to capture VTE risk data of the user when the casing is positioned against the user's chest.

4. The VTE, risk assessment system according to claim 1, wherein the casing is configured to capture VTE risk data of the user when the casing is positioned against the user's thoracic cage.

5. The VTE risk assessment system according to claim 1, wherein the casing is configured to capture VTE risk data of the user when the casing is positioned against the user's back.

6. The VTE risk assessment system according to claim 1, wherein the computing device further comprises a processor to execute a plurality of instructions pertaining to a VTE risk monitoring application, wherein the processor is configured to communicate one or more instructions to the user so that the user can position the casing on the user's body.

7. The VTE risk assessment system according to claim 1, wherein the classification model is trained to detect VTE.

8. The VTE risk assessment system according to claim 1, wherein the classification model is trained based on detected features of the IMU sensor.

9. The VTE risk assessment system according to claim 1, wherein the casing further comprises a heat-sensing camera to detect variations in a skin area temperature of the user resulting from variations in the blood volume changes in the skin area temperature of the user in response to venous hemodynamic changes in the user's lower limb.

10. The VTE risk assessment system according to claim 1,
    wherein the diaphragm comprises an enhancer unit for enhancing the one or more audio signals including the ability to amplify low-frequency auscultation signals in the one or more audio signals.

11. The VTE risk assessment system according to claim 1, wherein the casing further comprises a circuit board and a battery configured to supply electrical power to the circuit board.

12. The VTE risk assessment system according to claim 1 further comprising a second handheld electronic device worn by the user, comprising sensors to collect patient health data, wirelessly connected with the system, further comprising a wireless transceiver configured to establish a communication with the computing device to transmit VTE, risk data therebetween, wherein the computing device is configured to:
    detect, based on the classification model, VTE; and
    estimate, based on the regression model, a severity of a user's VTE risk.

13. The VTE risk assessment system according to claim 1, wherein the casing is configured as a patch with the ability to adhere to the user's body.

14. The VTE risk assessment system according to claim 1, wherein the casing further comprises storage memory for storing collected data.

15. The VTE risk assessment system according to claim 1, wherein the casing further comprises a plurality of electrodes comprising:
    a first ECG electrode placed on an outer surface of the casing; and
    a second ECG electrode and a third electrode placed on each side of the casing to facilitate a thumb and fingers of the user to be placed on the electrodes, wherein the plurality of electrodes are configured to capture data indicative of the VTE risk of the user.

16. The VTE risk assessment system according to claim 1,
    wherein the user is guided through instruction from the HED as to where to place the HED on the user's body.

17. The VTE risk assessment system according to claim 1, wherein the computing device identifies unique physiological markers of the user comprising previously collected sensor data.

18. The VTE risk assessment system according to claim 17, further comprising a database for storing one or more unique physiological markers of the user with one or more unique physiological markers of other users.

19. The VTE risk assessment system according to claim 12, wherein when there is the presence of a pre-determined severity of a user's VTE risk indicating a high probability of VTE, a message transmission containing the user's VTE risk is communicated to a healthcare professional.

20. The VTE risk assessment system according to claim 1, wherein the casing further comprises seismic and microphonic sensors to facilitate identification of common ambient environmental noise.

21. A vein thromboembolism (VTE) risk assessment system for use with a handheld electronic device (HED), the VTE risk assessment system comprising:
a HED with a casing having a shape adapted to secure the HED with the casing;
a plurality of electrodes comprising:
a first ECG electrode placed on an outer surface of the casing; and
a second ECG electrode and a third electrode placed on each side of the casing to facilitate a thumb and fingers of a user to be placed on the casing having the shape that is adapted to secure the HED, wherein the plurality of electrodes are configured to capture data indicative of a VTE risk of the user; and
a circuit board electrically connected with the plurality of electrodes, wherein the circuit hoard comprises:
a microphonic sensor to capture VTE one or more audio signals indicative of the VTE risk of the user;
a diaphragm to enhance auscultation signals;
a Photoplethysmography (PPG) sensor configured to measure blood volume changes in a skin area in response to venous hemodynamic changes in a limb;
an Inertial Measurement Unit (IMU) sensor to capture seismic and auscultation signals indicative of the VTE risk of the user, wherein the MU sensor comprises an IMU sensor signal-enhancing material to amplify seismic and auscultation signals; and
a microcontroller to transmit data indicative of the VTE risk of the user received from the plurality of electrodes, the microphonic sensor, the PPG sensor, and the IMU sensor to at least one of the following the HED and a computing device, wherein the computing device is configured to:
receive, in one or more temporal windows, a representation of one or more of the IMU sensor, the plurality of electrodes, the PPG sensor, and the microphonic sensor signal recorded by the casing;
detect features of the IMU sensor, the PPG sensor, and the microphonic sensor from at least one or more portions of the received representations falling within each of the one or more temporal windows;
identify patterns of the features of respective sensors from within the one or more portions based on at least a classification model or a regression model; and
calculate, basis the identified patterns, a probability of whether the one or more portions corresponds to a problem with the VTE risk of the user.

22. The VTE risk assessment system according to claim 21, wherein the HED secured with the casing comprises a display screen to display VTE diagnostic information derived from the VTE risk data received from the microcontroller.

23. The VTE risk assessment system according to claim 21, wherein the casing further comprises a lens configured to envelop a camera of the HED.

24. The VTE risk assessment system according to claim 23, wherein the lens is configured to block external light when the HED shines a light onto the skin of the user, wherein the light is used to help with the recording of one or more images of the skin of the user, and wherein the one or more images are analyzed based on machine learning in order to for provide insights into the VTE risk of the user.

25. The VTE risk assessment system according to claim 21,
wherein the casing further comprises one or more additional sensors to facilitate identification of common ambient environmental noise.

26. The VTE risk assessment system according to claim 25 where the one oar more additional sensors are selected from the following: a seismic sensor and an additional microphonic sensor.

27. The VTE; risk assessment system according to claim 21, wherein data indicating a high probability of VTE triggers a message transmission to a healthcare professional.

28. The VTE risk assessment system according to claim 21, wherein the user is guided through instruction from the HED where to place the device on their body.

29. The VTE risk assessment system according to claim 21, wherein the computing device identifies unique physiological markers of the user comprising previously collected sensor data.

30. The VTE risk assessment system according to claim 29, further comprising a database for storing one or more unique physiological markers of the user with one or more unique physiological markers of other users.

* * * * *